United States Patent [19]

Rizk

[11] Patent Number: 5,730,957

[45] Date of Patent: Mar. 24, 1998

[54] COMPOSITION, APPARATUS, AND METHOD FOR PROVIDING A SUPPLY OF WATER-BASED COOL MIXTURE

[76] Inventor: Nelly Kamel Rizk, 8 Knighton Close, S. Croydon, Surrey, United Kingdom, CR2 6DP

[21] Appl. No.: 446,608

[22] PCT Filed: Nov. 25, 1993

[86] PCT No.: PCT/GB93/02435

§ 371 Date: May 30, 1995

§ 102(e) Date: May 30, 1995

[87] PCT Pub. No.: WO94/13753

PCT Pub. Date: Jun. 23, 1994

[51] Int. Cl.$^6$ ..................... A61L 9/04
[52] U.S. Cl. ............. 424/45; 424/59; 424/65; 424/76.2; 424/401; 424/405; 512/1; 514/827; 514/829; 514/844
[58] Field of Search ............. 424/59, 65, 76.2, 424/401, 405, 45; 512/1; 514/827, 829, 844

[56] References Cited

U.S. PATENT DOCUMENTS 4,243,548  1/1981  Heeb et al. ..................... 252/305

FOREIGN PATENT DOCUMENTS 0414920  3/1991  European Pat. Off. .
1301618  5/1989  Japan .
4103526  4/1992  Japan .

Primary Examiner—Terressa Mosley

[57] ABSTRACT

The present invention provides a composition for providing a supply of water-based cool mixture, the temperature of which when utilised is lower than the ambient temperature and higher than the freezing point of water, which composition consists essentially of a mixture of water and a chemical compound selected from one or more of dimethyl ether, a homologue of dimethyl ether and a chemical derivative of dimethyl ether. The present invention also provides apparatus for providing a supply of water-based cool mixture, the temperature of which when utilised is lower than the ambient temperature and higher than the freezing point of water, which apparatus comprises a pressurized dispensing container, said container containing such a composition. The present invention further provides a method of cooling, e.g. of the body, a space, a surface, or a water based liquid by utilising such a composition or such an apparatus.

10 Claims, No Drawings

COMPOSITION, APPARATUS, AND METHOD FOR PROVIDING A SUPPLY OF WATER-BASED COOL MIXTURE

This invention relates to a composition and apparatus for providing a supply of water-based cool mixture and a method of providing a supply of water-based cool mixture.

Cool water or cool water-based mixture has numerous uses and applications in different aspects of life, whether for drinking, cosmetic, medical or other uses. The treatment of some medical conditions such as sunstroke/heatstroke which could be fatal, requires rapid cooling of the sufferer by application of cool water. The problem is to keep the water or water-based mixture cool for a long period of time without using refrigerator or power supply. Most known portable sources of cool water mixtures such as the thermos flask or similar are temporary, most working on the principal of providing an insulated medium for the cool water-based mixture which was previously cooled or to include previously frozen ice packs.

Some of the situations which would benefit from the provision of a supply, preferably portable, of water-based cool mixture are discussed below:

The problems associated with living in hot climates are familiar. When the heat reaches its peak, usually around mid day, life is rather uncomfortable. The body feels the heat and the sweat producing system is unable to cope with the excess heat, so the body feels hot. A cool drink, a shower, or a plunge in a pool or the sea immediately relieves the problem, but this may not always be feasible or possible.

Sports players or individuals involved in vigorous muscular activity warm up quickly, the more so during hot weather. They would benefit from a convenient method to cool them quickly and to relieve them from the body heat.

Sunstroke or heatstroke can affect individuals if they expose themselves to the sun or heat longer than their body can cope with. A method is needed to protect individuals from excess heat and to cool them down quickly before they are seriously sick as a result of sunstroke or heatstroke.

One widely used method of treating sunstroke/heatstroke is to quickly apply cool water on the sufferers to cool them down. Cool water may not be readily available especially in hot climates. Readily available, reliable cool water supply near a sufferer may make the difference between life and death.

Burns and sunburns require similar treatment i.e. apply cool water on the affected area of the skin. The lack of cool water supply may cause difficulties.

When the body suffers from fever, any medication given usually takes time to work, the time needed for the medication to be absorbed by the body's natural systems. Moreover it may be difficult in some cases to administer the right medication due to some medical complications present at the time. A method is needed to lower the body temperature quickly while medication has time to work, or to replace medication where necessary.

Women experiencing menopause and in some cases men, may suffer from hot flushes and would benefit from a method that would offer them rapid heat relief.

Motor vehicles parked in the sun turn into 'scorching ovens', the steering wheel becoming too hot to touch, and the seats, the seat belt buckles and child's seat becoming painfully hot. A pressing need arises to reduce the temperature of the passenger compartment on entering and to cool the hot surfaces to render them safe, in particular to the touch of small children.

Enclosed spaces often become uncomfortably hot and the use of fans or air-conditioning has hitherto been necessary. Air-conditioning is a high power electrical load and needs a specially adapted power supply unit. Fans produce their cooling effect by increasing the speed of air movement which increases the rate of sweat evaporation, so the body feels less hot. In the absence of a suitable power supply the problem persists. A method is needed to lower the temperature of the enclosed spaces.

In all of the above situations, cooling may be achieved by the employment of cool water or water-based mixture which results in an instant heat relief, cool treatment/prevention of a medical condition or lowering the temperature as the application entails. Some applications require the water-based mixture to be cooler than others e.g. treatment for sunburn, minor burns require cooler water-based mixture than lowering the body fever which is treated by applying slightly cool water-based mixture.

The above leads to the conclusion that a method is required to provide a supply of water-based cool mixture, preferably portable, delivered at a temperature below ambient in hot climates and equally important it must not reach freezing levels in order for it to be effective in addressing the above situations. Ideally the temperature of the cool water-based mixture should vary between approx. 18° C. and 23° C. in an ambient varying between approx. 25° C. and 45° C. respectively. The method must also include a facility for controlling the temperature of the delivered water-based mixture in order to suit the different applications whilst accommodating the varying ambient temperatures.

A few of the above issues have been addressed in U.S. Pat. No. 5,062,269 "Disposable Body Cooler" and in Australian Patent Specification No. 63943/90 "Evaporative Cooler for Human Body and Other Articles". The present inventors are also aware of French Patent Specifications Nos 2118398 and 2384218, and of the European Patent Specification No. 0334814 B1 and 0414920 A1. The latter describes a foam-forming aerosol preparation, which comprises Dimethyl Ether and water and is essentially flammable (since the flammable content in the preparation exceeds 45% by weight). The inventor of the present invention believes however that the present invention is an improvement over the methods and compositions disclosed in those Specifications. The present invention therefore has as an object the amelioration of the above problems.

According to a first aspect of the present invention there is provided a composition for providing a supply of water-based cool mixture, the temperature of which when utilised is lower than the ambient temperature and higher than the freezing point of water, which composition consists essentially of water and dimethyl ether. According to a second aspect of the present invention there is provided an apparatus for providing a supply of water-based cool mixture, the temperature of which mixture when utilised is lower than the ambient temperature and higher than the freezing point of water, which apparatus comprises a pressurized dispensing container containing a composition, which composition consists essentially of water and dimethyl ether.

According to a third aspect of the present invention there is provided a method of providing a supply of water-based cool mixture, the temperature of which when utilised is lower than the ambient temperature and higher than the freezing point of water, which method comprises employing a composition as hereinbefore defined.

Throughout this specification and the claims the following terms shall mean:

Pressurized: subjected to a pressure above atmospheric pressure.

Body: Human body, including limbs, head, face, neck, etc.

Cooling: Reducing the temperature or elimination/absorption of heat, whether inherent heat or heat acquired as a result of external factors e.g. hot weather, without achieving freezing conditions.

Depending on the desired application, the composition of the cooling mixture may comprise from 3% to 44% by weight of dimethyl ether and from 97% to 56% water or demineralised water. The invention is not however to be limited thereto. A material such as a solvent may be included to improve the miscibility/solubility of dimethyl ether in the water or to modify the vapour pressure. The amount of solvent included (if present) is preferably from approximately 1% to approximately 15% by weight of the composition.

Minor amounts of one or more of the following may be included in the composition of the present invention as desired:

fragrance
aromatic alcohol
emulsifier
anti-oxidant
corrosion inhibitor
antiseptic agent
disinfectant
antibiotic
edible flavouring ingredients Furthermore, one or more of the following components may be included to combine the cooling function with the intended function of the included component:

ultra-Violet absorber/sun-screening composition
sun-tanning composition
deodorant/antiperspirant composition
insect-repellent composition
soap composition
air-freshener composition
antiseptic agent
disinfectant
antibiotic The pressurized container of the apparatus of the present invention may be adapted to dispense therefrom the water-based mixture of the present invention by virtue of the internal pressure of the container or by means of a pump action or a battery-operated system. A propellant for dispensing the mixture from the container may be dimethyl ether if suitable as a propellant, or a pressurized gas.

As has been indicated, the method, apparatus and composition may be used for cooling a body, a space or a surface.

An embodiment of the composition and apparatus of the present invention will now be described, by way of example only. In a preferred embodiment of the invention a mixture of water and dimethyl ether (known commercially as DME or sometimes as methane oxybis, methyl ether or methoxyethane) is contained within an aerosol dispenser. Dimethyl ether is fully miscible with water, forming one clear liquid phase when the percentage of dimethyl ether in water is no more than approximately 34% by weight at 20° C. The spray is applied onto the body, into the confined hot space or onto the hot surface and cooling thereof is achieved.

The quick cooling takes place as a result of:

(1) The dimethyl ether ( boiling point: −24.9° C.) turning into gas by absorbing its heat of transformation from the water and the surroundings. The dimethyl ether miscibility in water allows the dimethyl ether molecules to absorb the heat of transformation from the adjacent water molecules, hence the water is cooled rapidly. The dimethyl ether acts as a cooling agent as well as a propellant. The water-based mixture is discharged at a temperature much lower than the ambient temperature, hence relative cooling is achieved.

(2) The cool water-based spray rapidly evaporating when it touches a hot surface or is applied at high ambient temperatures, thus absorbing the latent heat of vaporization from the surrounding surfaces and the atmosphere. The higher is the ambient temperature the faster is the evaporation and thus the faster the fall in temperature.

The latent heat of evaporation of water is $22.6 \times 10^5$ J/Kg, which is high compared with the latent heat of vaporization of other solvents miscible with dimethyl ether such as alcohol, acetone, methylal etc., hence resulting in a higher temperature drop in the surrounding surfaces and atmosphere.

(3) When the spray touches the body, it has a pleasant quick cooling effect. No matter how high is the ambient temperature, nor how long the pressurized container of this invention may have been exposed to that temperature, the spray still feels relatively cool when applied.

(4) When the cool water mixture is employed as a spray, control of the spray temperature, when falling on the object, is achieved by varying the spray distance and spray time. The spray distance is directly proportional to the temperature i.e. the longer the spray distance the higher the temperature (less cooling) and the shorter the spray distance the lower the temperature (more cooling). The spray time is inversely proportional to the temperature i.e. the longer the spray time the lower the temperature (more cooling) and the shorter the spray time, the higher the temperature (less cooling). Ideally the spray distance should vary between 7 cm and 30 cm approximately. The ambient temperature may decide the spray distance and spray time e.g. on very hot days the spray distance may be shortened and spray time is increased to achieve more cooling. On the other hand the nature of the application may decide the spray distance.

The properties of a simple miscible mixture of dimethyl ether and water (i.e. up to approximately 34% by weight dimethyl ether at 20° C.) are excellent for the cooling applications. The properties of the mixture are:

Non-flammable
Non toxic, safe to use in confined areas with reduced ventilation.
Safe to use on the skin.
Does not discolour fabrics.
Free from chlorofluorocarbons which deplete the earth's ozone layer.
Stable mixture.
Low VOC (Volatile Organic Compound) emission.
Produces a pleasant cooling effect on the skin, during hot weather, i.e. not too cold so as to cause a shock especially to old people and small children.
Safe vapour pressure within an appropriate aerosol dispenser at high ambient temperatures.

There may be a need to lower the vapour pressure of the dimethyl ether and water mixture. The higher is the water concentration the lower is the pressure. Alternatively an amount of a suitable solvent such as alcohol, acetone, methylal may be added to the mixture to achieve a lower vapour pressure. Solvents may be also added to increase the miscibility of dimethyl ether in water to achieve a concentration in water of greater than 34% by weight of dimethyl ether. The amount of solvent included is preferably from approximately 1% to approximately 15% by weight of the composition.

The following formulation examples are given to further illustrate the present invention. However the invention is not limited thereto. The cooling property of each has been tested and has been found to have, save for minor differences, satisfactory results.

| INGREDIENTS | PERCENT BY WEIGHT |
|---|---|
| EXAMPLE 1 | |
| Water | 7.00 |
| Dimethyl Ether | 30.00 |
| | 100.00 |
| EXAMPLE 2 | |
| Water | 69.00 |
| Dimethyl Ether | 30.00 |
| Fragrance/aromatic alcohol | 1.00 |
| | 100.00 |
| EXAMPLE 3 | |
| Water | 60.00 |
| Dimethyl Ether | 34.00 |
| Ethyl alcohol | 5.00 |
| Aromatic alcohol | 1.00 |
| | 100.00 |
| EXAMPLE 4 | |
| Water | 59.00 |
| Dimethyl Ether | 30.00 |
| Methylal | 10.00 |
| Fragrance/aromatic alcohol | 1.00 |
| | 100.00 |
| EXAMPLE 5 | |
| Water | 57.00 |
| Dimethyl Ether | 33.00 |
| Methylal | 5.00 |
| Acetone | 4.00 |
| Aromatic alcohol | 1.00 |
| | 100.00 |
| EXAMPLE 6 | |
| Water | 74.50 |
| Dimethyl Ether | 24.00 |
| Pressurised gas (Nitrogen) | 0.50 |
| Fragrance/aromatic alcohol | 1.00 |
| | 100.00 |

Applications and uses for the composition, apparatus and method of the present invention include, but are not confined to, the following:

(1) COOLING OF THE BODY:

When the water-based cool mixture is applied as a spray on the body, the dimethyl ether vaporizes and in doing so absorbs the heat from the water and from the surroundings. The water remains and is cooled by the dimethyl ether vaporizing. The cooling effect upon the body is therefore not only that of cool water on the body, the water itself then evaporates thus further to cool the body. The human body's normal temperature of approx. 37° C. helps to quickly vaporize the remaining water, thus instant cooling is achieved. The method, composition and apparatus of the present invention may be used for cooling the body during hot weather, for medical applications such as to reduce the temperature of the body in the event of fever, to protect from and to treat sunstroke and heatstroke or to offer heat relief for those who experience hot flushes. The method may be also used to offer heat relief for those exerting strenuous muscular activity such as construction workers, dancers or those practising sports.

Burns and sunburns may also be treated by applying the water-based cool mixture to the affected area, which quickly cools down thus soothing it and reducing the pain.

Other body cooling applications include but are not limited to: relief from tension, stress, relief from itchy skin and preventing/treating prickly heat condition. In general the method may also be employed to replace cool compresses whenever the need for them arises.

Sterilised water may be used instead of ordinary water or demineralised water for medical applications.

The required level of cooling may be achieved by varying the spray distance and time as explained earlier.

(2) COOLING OF HOT CONFINED SPACES:

Practically instant cooling is achieved by applying a spray of the mixture a number of times as needed in the confined space. The spray, in the high ambient temperatures, evaporates quickly thus absorbing the heat from the surroundings. The rate of evaporation increases in the presence of a fan or a controlled air draft. The higher is the ambient temperature the higher is the temperature drop.

(3) REDUCING THE TEMPERATURE OF THE PASSENGER COMPARTMENT OF A VEHICLE AND OF HOT SURFACES INSIDE THE SAID COMPARTMENT:

When a vehicle is parked in high ambient temperatures, the temperature of the passenger compartment is usually much higher than the external ambient temperature. When one door is opened and a spray of the mixture is applied a number of times as needed inside the passenger compartment, on the steering wheel and other hot surfaces, the temperature inside the vehicle is reduced to a bearable level and the hot surfaces become bearable to touch. The water and dimethyl ether evaporate rapidly at the high ambient thus lowering the temperature within the vehicle.

(4) PROVIDING A SUPPLY OF COOL WATER-BASED DRINKS

The present invention may be exploited by the drinks industry to provide cool water-based drinks. Dimethyl ether is incorporated into the water-based drinks, maintained under pressure. The pressure is released and dimethyl ether is allowed to evaporate before the drinks are consumed. In effect the drink dispenser is opened and dimethyl ether is allowed to escape, in so doing cooling of the remaining mixture is achieved.

VARIATION ON THE APPLICATION OF THE COOLING OF THE BODY:

(1) A suitable ultra-violet absorber composition and/or sun-screening agent may be added to the water-based mixture described herein. The resulting mixture has a combined function of cooling and refreshing the body as well as protecting the skin from the harmful rays of the sun.

(2) A suitable deodorant and/or anti-perspirant composition may be added to the water-based mixture described herein. The resulting mixture has a combined function of cooling and refreshing the body as well as controlling perspiration.

(3) A suitable insect-repellent composition may be added to the water-based mixture described herein. The resulting mixture has a combined function of cooling and refreshing the body as well as repelling insects.

(4) A suitable sun-tanning composition may be added to the water-based mixture described herein. The resulting mixture has a combined function of cooling and tanning the body.

(5) A suitable soap composition may be added to the water-based mixture described herein. The resulting mixture has a combined function of cooling and refreshing the body while the soap is applied on the skin.

(6) One or more of a suitable antiseptic agent, a disinfectant and an antibiotic may be added to the water-based mixture described herein. The resulting mixture has a combined function of cooling and disinfecting/combating disease.

VARIATION ON THE APPLICATION OF THE QUICK COOLING OF THE ATMOSPHERE IN CONFINED SPACES:

A suitable air freshener composition may be added to the water-based mixture described herein. The resulting mixture has a combined function of cooling small rooms or confined areas and freshening the air as well. A disinfectant may be also incorporated.

The present invention includes within its scope all variations and modifications that would be apparent or obvious to one skilled in the art and the scope of the invention is to be determined only by the extent of the accompanying claims.

I claim:

1. A non-flammable composition for providing a supply of water-based cooling mixture, the temperature of which cooling mixture when utilised is lower than the ambient temperature and higher than the freezing point of water, which composition consists essentially of a mixture of water and dimethyl ether.

2. A composition according to claim 1, which further comprises a material, the amount of which does not exceed 15.0% by weight of the composition, to increase the miscibility or solubility of the dimethyl ether in the water or to modify the vapour pressure of the composition.

3. A composition according to claim 2, wherein the said material is selected from an alcohol, acetone or methylal.

4. A composition according to claim 1, wherein the dimethyl ether is present in an amount of from 28% to 35% by weight of the composition.

5. A composition according to claim 1, wherein minor amounts of one or more of the following are included: fragrance, aromatic alcohol, emulsifier, anti-oxidant, corrosion inhibitor, antiseptic agent, disinfectant, antibiotic and edible flavouring ingredients.

6. A composition according to claim 5, wherein one or more of the following compositions is included to combine the cooling function with the intended function of the included composition: ultra-violet absorber/sun-screening composition, sun-tanning composition, deodorant/anti-perspirant composition, insect-repellant composition, soap composition, air-freshener composition, antiseptic agent, disinfectant and antibiotic.

7. Apparatus for providing a supply of water-based cool mixture, the temperature of which when utilised is lower than the ambient temperature and higher than the freezing point of water, which apparatus comprises a pressurized dispensing container, said container containing a composition as claimed in claim 1.

8. Apparatus according to claim 7, wherein the dimethyl ether of said composition is employed as a propellant.

9. Apparatus according to claim 7, wherein a pressurized gas is employed as a propellant.

10. An apparatus according to claim 7, wherein the apparatus is adapted for use for cooling.

* * * * *